United States Patent
Schade et al.

(10) Patent No.: US 10,488,253 B2
(45) Date of Patent: Nov. 26, 2019

(54) SPECTROMETRIC MEASURING HEAD FOR FORESTRY, AGRICULTURAL AND FOOD INDUSTRY APPLICATIONS

(71) Applicant: Deere & Company, Moline, IL (US)

(72) Inventors: Peter Schade, Bad Dürkheim (DE); Helge Klein, Kaiserslautern (DE)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 16/052,317

(22) Filed: Aug. 1, 2018

(65) Prior Publication Data

US 2019/0056265 A1  Feb. 21, 2019

(30) Foreign Application Priority Data

Aug. 17, 2017 (DE) .......... 10 2017 214 352

(51) Int. Cl.
*G01J 3/02* (2006.01)
*A01D 41/127* (2006.01)
(Continued)

(52) U.S. Cl.
CPC ........ *G01J 3/0291* (2013.01); *A01D 41/1277* (2013.01); *A01D 43/085* (2013.01); *G01J 3/021* (2013.01); *G01J 3/0208* (2013.01); *G01J 3/0229* (2013.01); *G01J 3/0232* (2013.01); *G01J 3/0294* (2013.01); *G01J 3/10* (2013.01); *G01J 3/28* (2013.01); *G01J 3/42* (2013.01); *G01J 3/502* (2013.01); *G01N 21/314* (2013.01); *G01N 21/359* (2013.01); *G01N 21/3563* (2013.01);
(Continued)

(58) Field of Classification Search
CPC ........ G01J 3/0291; G01J 3/0208; G01J 3/021; G01J 3/0229; A01D 41/1277; A01D 43/085; G01N 21/314; G01N 21/3563; G01N 21/359; G01N 2021/3155
See application file for complete search history.

(56) References Cited

U.S. PATENT DOCUMENTS 5,568,266 A * 10/1996 Ciza .......................... G01J 3/02
  250/226
7,804,588 B2 * 9/2010 Kormann ........... G01N 21/3563
  356/328

(Continued)

FOREIGN PATENT DOCUMENTS

DE        19922867 A1   11/2000
DE     102004048103 A1    4/2006
(Continued)

OTHER PUBLICATIONS

Search Report issued in counterpart application No. EP18188907.2, dated Jan. 14, 2019 (8 pages).

Primary Examiner — Hina F Ayub

(57) ABSTRACT

A spectrometric measuring head for forestry, agricultural and food industry applications comprises a housing having a window and a spectrometer that is arranged inside the housing and comprises a dispersive element and a sensor, a first light source for exposing a sample to light, which reaches the spectrometer through the window after having been transmitted and/or reflected by the sample, and a standard that can be exposed to light to provide a reference for the spectrometer, which standard can be exposed to light by a light source arranged in the housing.

20 Claims, 2 Drawing Sheets

(51) Int. Cl.
*A01D 43/08* (2006.01)
*G01N 21/31* (2006.01)
*G01N 21/3563* (2014.01)
*G01N 21/359* (2014.01)
*G01J 3/10* (2006.01)
*G01J 3/28* (2006.01)
*G01J 3/42* (2006.01)
*G01J 3/50* (2006.01)
*G01N 21/85* (2006.01)
*G01N 21/84* (2006.01)

(52) U.S. Cl.
CPC ...... *G01N 21/85* (2013.01); *G01J 2003/2866* (2013.01); *G01N 2021/3155* (2013.01); *G01N 2021/8466* (2013.01); *G01N 2201/0216* (2013.01)

(56) References Cited

U.S. PATENT DOCUMENTS

| | | | |
|---|---|---|---|
| 2005/0226548 A1* | 10/2005 | Durkin | G01N 21/31 385/12 |
| 2008/0094626 A1* | 4/2008 | Becker-Ross | G01J 3/02 356/328 |
| 2008/0186487 A1 | 8/2008 | Kormann et al. | |
| 2010/0245602 A1* | 9/2010 | Webster | H04N 5/211 348/208.4 |
| 2011/0299083 A1* | 12/2011 | Yokoyama | G01J 3/02 356/432 |
| 2013/0258341 A1* | 10/2013 | Day | G01J 3/0291 356/402 |
| 2017/0293812 A1* | 10/2017 | Itoh | G01N 21/21 |

FOREIGN PATENT DOCUMENTS

| | | |
|---|---|---|
| DE | 102007011324 A1 | 9/2008 |
| DE | 102009017210 A1 | 10/2009 |
| DE | 102010041793 A1 | 4/2012 |
| EP | 1637850 A1 | 3/2006 |
| WO | 0131304 A1 | 5/2001 |

* cited by examiner

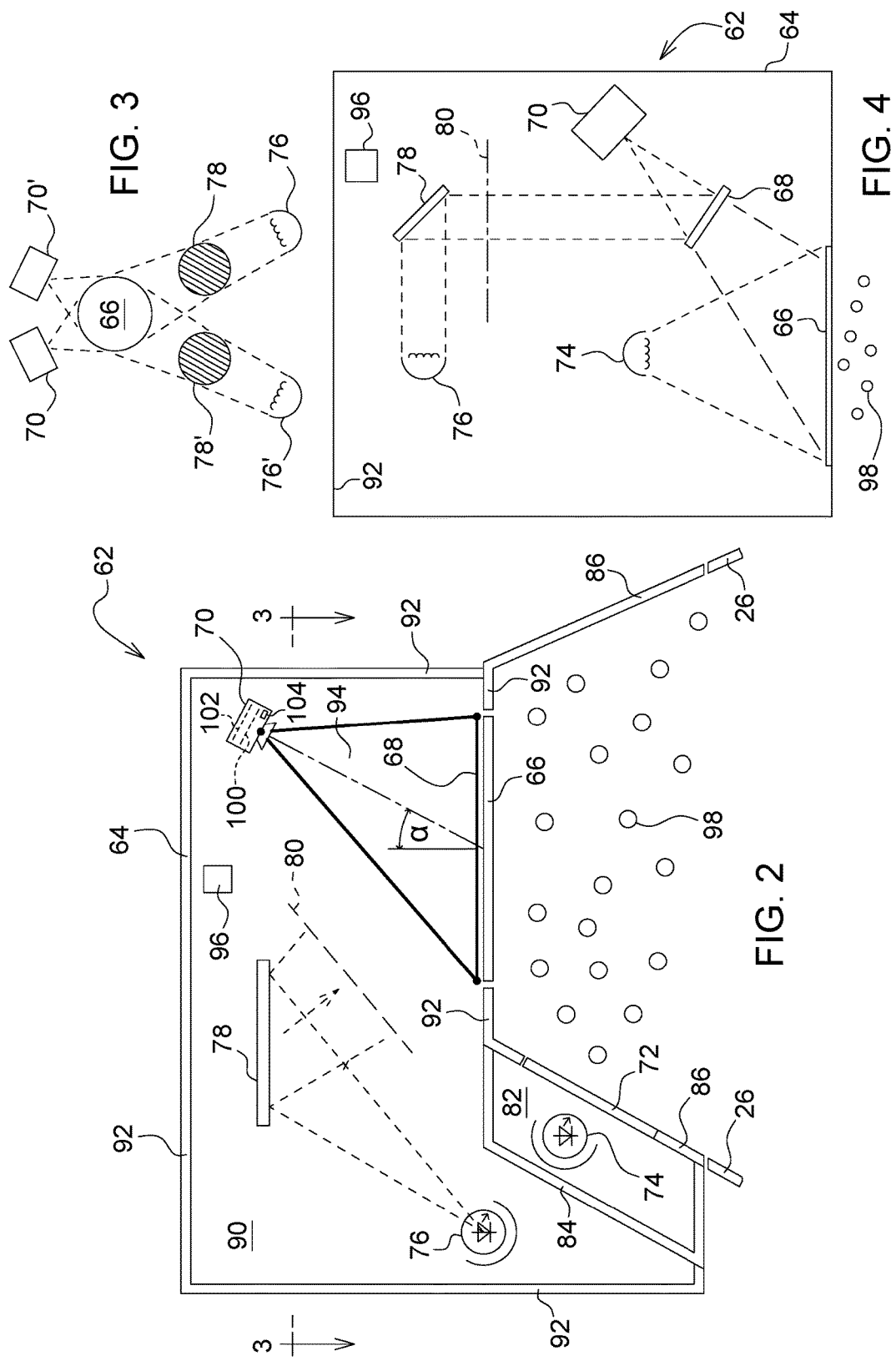

SPECTROMETRIC MEASURING HEAD FOR FORESTRY, AGRICULTURAL AND FOOD INDUSTRY APPLICATIONS

FIELD OF THE INVENTION

The invention relates to a spectrometric measuring head for forestry, agricultural and food industry applications. More particularly, it relates to spectrometric harvesting heads having a housing with a window and a spectrometer that is arranged inside the housing and comprises a dispersive element and a sensor.

BACKGROUND OF THE INVENTION

There is an interest in various types of agricultural work in detecting the proportion of certain content substances in samples by sensing means. In addition to crop material, possible samples also include soil samples, liquid manure and milk. The detected content substances can be used to assess the sample (particularly crops or other agricultural products) monetarily, or the sensed values are saved for purposes of precision agriculture, e.g. for customized fertilizer application, or they can be used for controlling application amounts, for example from a liquid manure tank.

A customary technique for determining content substances in the agricultural field is near-infrared spectroscopy, in which broadband light is applied to the sample and the light reflected from or transmitted by the sample is decomposed spectrally and analyzed. Measuring heads based on such technology are described in DE 199 22 867 A1, WO 01/31304 A1 and DE 10 2004 048 103 A1 for example. They use a dispersive element (prism or grating) for spectral decomposition of the light and a light detector to be able to sense the individual wavelengths simultaneously. These measuring heads use movable elements for moving a white standard into the beam path to provide a reference.

One problem addressed by the invention is providing a spectroscopic measuring head that requires fewer movable elements for providing a reference.

SUMMARY OF THE INVENTION

In accordance with one aspect of the invention, a spectroscopic measuring head for agricultural applications comprises a housing having a window and a spectrometer that is arranged inside the housing and comprises a dispersive element and a sensor; a first light source arranged inside the housing, for exposing a sample to broadband light, wherein the first light source and the housing are arranged such that the light from the first light source reaches the spectrometer through the window after it has been transmitted or reflected by the sample; and a standard which can be exposed to light to provide a reference for the spectrometer, which standard can be exposed to broadband light by a second light source arranged in the housing.

In other words, the sample may be illuminated in a conventional manner by a first light source, arranged inside or outside the housing, which contains a window and a spectrometer.

The reference for the spectrometer may be provided by a second light source arranged in the housing. In this manner, elaborate means of the type provided in the prior art, which require an externally operated drive mechanism to move the standard into the beam path of the first light source, are superfluous.

A partially transmissive mirror may be arranged on the window or between the window and the spectrometer and reflect light reflected from the standard into the spectrometer.

Between the second light source and the spectrometer (more particularly between the mirror and the standard) it may be possible to arrange a filter having an electrically controllable transmissivity.

The spectrometer may be configured as a micro-electromechanical system (MEMS).

The optical axis of the spectrometer may enclose an angle different from zero with the surface normal line of the window.

The arrangement may further include an additional spectrometer, which may be offset at an angle relative to the first spectrometer, and which may be in the housing. The two spectrometers may have identical, partially overlapping, or different spectral measuring ranges.

The light sources and optionally the filter may be connected to a controller that can be operated in normal measuring operation to switch on the first light source and switch off the second light source and/or switch the filter to be non-transmissive, and may be operated to switch off the first light source and switch on the second light source and/or switch the filter to be transmissive to provide a reference for the spectrometer.

The measuring head may be used for various measuring tasks in forestry, the food industry or agriculture. The measuring head may be used in stationary or mobile mode to examine a stationary sample, or the sample can be moved past the measuring head (or vice versa), e.g. on an agricultural field, to evaluate crop or soil properties and evaluate content substances in the crop or soil based on the detected spectra. It may be used for examining the content substances (e.g. potassium or phosphorus) of other gaseous, solid or liquid samples (e.g. liquid manure, milk, liquid fertilizer, sprayed agents, standing plants) either as a handheld device or attached to a machine for transporting and/or applying a fluid (e.g. a field sprayer or a liquid manure tank). The detected content substances and/or data of the sample derived therefrom may be mapped in a georeferenced manner by a computer device and/or used for actuating an agricultural machine, e.g. for controlling the application of fertilizers, liquid manure, spraying agents, seeds, silage additives, etc.

In accordance with another aspect of the invention, a spectrometric measuring head is provided for forestry, agricultural and food industry applications, comprising: a housing having a window and a spectrometer that is arranged inside the housing and comprises a dispersive element and a sensor, a first light source for exposing a sample to light, which reaches the spectrometer through the window after having been transmitted and/or reflected by the sample, and a standard that can be exposed to light to provide a reference for the spectrometer, wherein the standard can be exposed to light by a light source arranged in the housing.

The first light source may be arranged inside or outside the housing.

A partially transmissive mirror may be arranged on the window or between the window and the spectrometer and may reflect light reflected from the standard into the spectrometer.

A filter having an electrically controllable transmissivity may be arranged between a second light source and the spectrometer and more particularly between a mirror and the standard.

The spectrometer may be designed as a micro-electromechanical system (MEMS).

The optical axis of the spectrometer may enclose an angle different from zero with respect to surface normal lines of the window.

The spectrometric measuring head may have at least one additional spectrometer arranged in a housing and offset relative to the spectrometer.

The spectrometer and the at least one additional spectrometer may have identical, partially overlapping or different spectral measuring ranges.

The light source and optionally a filter may be connected to a controller which is operable in normal measuring operation to switch on the first light source and switch off a second light source or switch the filter to be non-transmissive, and may be operable to switch off the first light source and switch on the second light source or switch the filter to be transmissive in order to provide a reference for the spectrometer.

In accordance with another aspect of the invention an agricultural machine may have a spectrometric measuring head.

BRIEF DESCRIPTION OF THE DRAWINGS

Two embodiments of the invention, described in detail below, are shown in the drawings, wherein the reference numbers may not be used for a limiting interpretation of the claims:

FIG. 2 shows a sectional view through the measuring head along the line 2-2 of FIG. 1, FIG. 3 shows a sectional view through the measuring head along the line 3-3 of FIG. 2.

FIG. 4 shows a sectional view through a second embodiment of a measuring head.

DETAILED DESCRIPTION OF THE PREFERRED EMBODIMENTS

Figure 1:
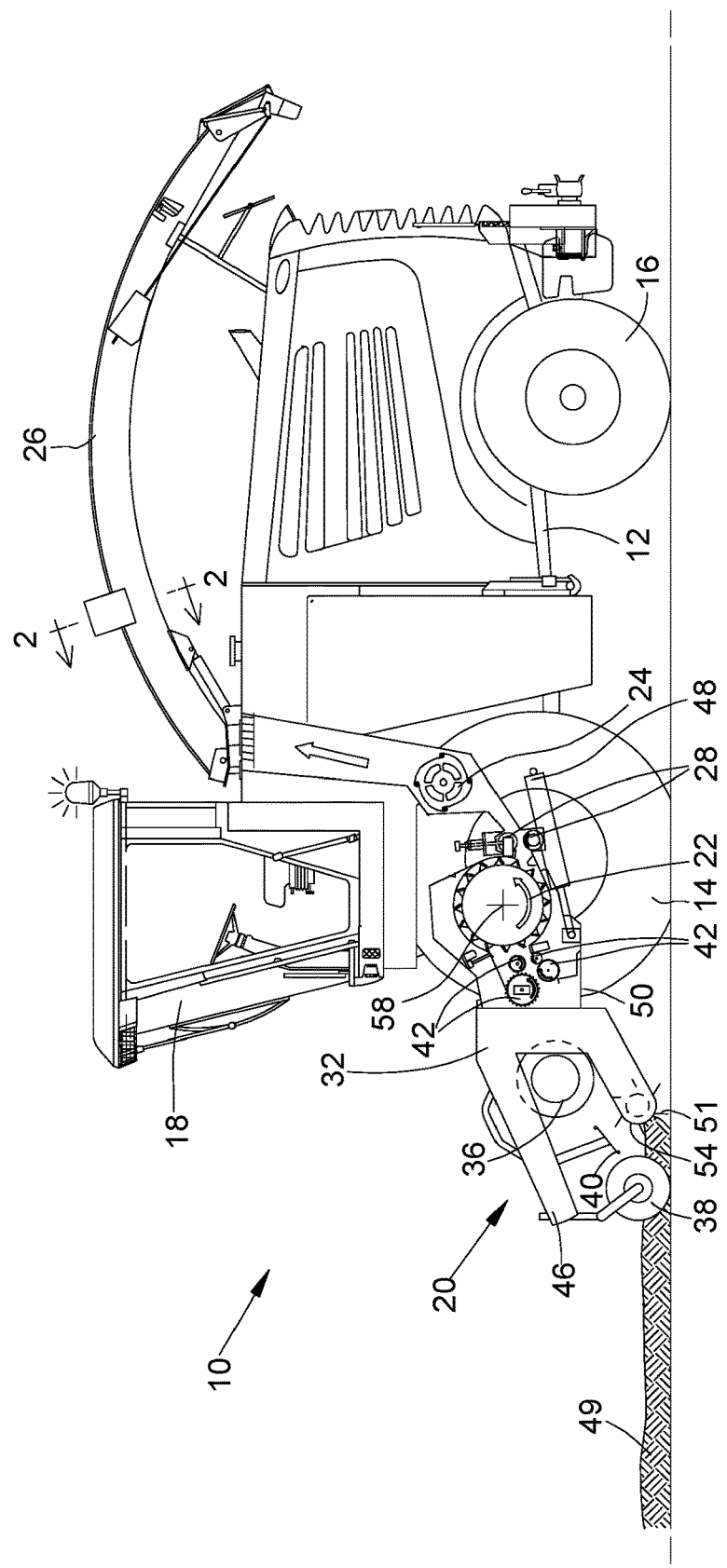
FIG. 1 shows a side view of a harvesting machine with a spectrometric measuring head.

FIG. 1 presents a self-propelled harvester 10 in the form of a self-propelled forage harvester. The harvester 10 is constructed on a frame 12 that is supported by driven front wheels 14 and steerable rear wheels 16. The harvester 10 is operated from a driver's cab 18, from which a harvesting header 20 can be seen. Crop such as grass or the like picked up from the ground by means of the harvesting header 20 is fed, via an intake conveyor 42 having pre-pressing rollers arranged inside an intake housing 50, which removably supports the harvesting header 20 on the front side of the forage harvester 10, to a chopping drum 22 that chops the crop into small pieces and transfers it to a conveying unit 24. Via an ejection chute 26, rotatable about an approximately vertical axis and having an adjustable inclination, the material leaves the harvesting machine 10 to a trailer moving alongside. A post-comminution device 28 having two grain processor rollers, through which the crop to be transported by the conveying unit 24 is fed tangentially, is located between the chopping drum 22 and the conveying unit 24.

The harvesting header 20 is designed as a pickup. The harvesting header 20 is constructed on a frame 32 and supported on the ground via support wheels 38 on each side, which are fastened by a respective beam 46 to the frame 32. The task of the harvesting header 20 is to pick up crop scattered on the ground of the field or deposited in a swath 49 and to feed it to the harvesting machine 10 for further processing. For this purpose, the harvesting header 20 is moved over the field during harvesting operation at a slight distance from the ground, while it is raised for transport on a road or on trails by means of an actuator 48 in the form of a hydraulic cylinder that pivots the intake housing 50 and the harvesting header 20 mounted thereon about the axis of rotation 58 of the chopping drum 22. The actuator 48 is also used for adjusting the height of the crop pickup 54 above the ground, or for adjusting the contact pressure of the support wheels 38 on the ground. The harvesting header 20 includes a cross-conveying auger 36, which conveys the picked-up crop material from the sides of the harvesting header 20 to a discharge opening, not shown, located in the center, which the intake conveyor 42 adjoins. The harvesting header 20 further comprises a crop pickup 54, which is rotationally driven (like the cross-conveying auger 36) and is arranged underneath the cross-conveying auger 36 and lifts the crop material from the ground with its teeth 51 to transfer it to the cross-conveying auger 36. A hold-down 40 in the form of a panel arranged above the crop pickup 34 is also mounted on the frame 32.

Directional indications such as to the side, below and above in the text below relate to the forward-moving direction V of the harvesting header 20 and the harvesting machine 10, which runs to the right in the figures.

A spectrometric measuring head 62, which is shown in more detail in FIGS. 2 and 3, is mounted on the ejection chute 26. The measuring head 62 comprises a housing 64 with upper, lateral and lower walls 92. A window 66, preferably consisting of sapphire glass, is formed in the lower wall 92. Inside the housing 64, immediately above the window 66, a partially transmissive mirror 68 is arranged, which could also be implemented as a vapor-deposited layer on the window 66 or could be arranged at a distance from the window 66. The sensitive region (aperture 94) of the spectrometer 70, which can be designed as a micro-electromechanical system, is oriented toward the window 66. The optical axis of the spectrometer 70 encloses an angle α with the surface normal lines of the window 66 that can be several multiples of 10°; it would also be conceivable, however, to align the optical axis of the spectrometer 70 with the surface normal lines of the window 66. The spectrometer 70 comprises a dispersive element 100, adjustable by an actuator 104, and a sensor 102. The actuator 104 makes it possible for the sensor 102 to receive defined wavelength ranges of the incident light that are specified by the actuator 104, while the other wavelength ranges do not reach the sensor 102.

The sample 98, which is comminuted crop material flowing through the ejection chute 26 in the illustrated example, is illuminated by a first light source 74, which is arranged inside an assigned space 82 that is separated by a wall 84 from the interior of the housing 64 and irradiates the sample 98 through an illumination window 72, which preferably also consists of sapphire glass. The first light source 74 can be a halogen lamp or a light-emitting diode or any other desired light source.

The housing 64 comprises in the lower region thereof walls 86 that are shaped as an extension of the lateral walls of the ejection chute 26 and are detachably connected thereto. After removing the measuring head 62, the portion of the ejection chute 26 otherwise closed off by the measuring head 62 can be closed by a cover (not shown).

To provide a reference for the spectrometer 70, a second light source 76, which can likewise be a halogen lamp or a light-emitting diode or any other desired light source, is arranged inside the housing 64. The second light source 76 illuminates a standard 78, a diffusely reflective white surface. The light reflected from the standard 78 reaches the partially reflective mirror 68 through an (optional) filter 80 having an electrically controllable transmissivity and is reflected by the mirror to the spectrometer 70. Thereby the standard 78 is imaged via the partially reflective mirror 68 into the spectrometer 70.

A controller 96 is connected to the light sources 74, 76 and controls the brightness thereof, as well as the transmissivity of the filter 80. In normal operation, the first light source 74 is switched on and the second light source 76 is switched off and/or the filter 80 is non-transmissive. The light from the first light source 74, lying in the visible and/or (near) infrared spectral range, that passes through the illumination window 72 strikes the sample 98 and is reflected therefrom and partially also transmitted and, through the window 66 and the partially transmissive mirror 68, reaches the spectrometer 70, in which it is successively decomposed into spectral components and the latter are detected by the sensor 102. Spectra are thus obtained, on the basis of which the amount of certain content substances in the sample 98 is calculated by the controller 96 or some other evaluation unit with reference to calibration data. To provide a reference for the spectrometer 70, the first light source 74 is switched off by the controller 96 and the second light source 76 is switched on and/or the filter 80 is switched to be transmissive. Then the light reflected by the standard 78 reaches the spectrometer 70, the spectral sensitivity of which can now be calibrated by the controller 96 or some other evaluation unit. The filter 80 can be designed as a polarization filter (known from display technology for example) and can be arranged between the standard 78 and the partially transmissive mirror 68, or between the mirror 68 and the spectrometer 70, and can make it possible to control the transmitted light quantity by using a voltage signal. In this case, it is possible to operate the second light source 76 at a constant light intensity during the reference-provision process (and optionally also during the measuring process).

For the reference-provision process as described, it makes sense not to illuminate the sample 98 via the illumination window 72, because otherwise light could reach the spectrometer 70 via the partially transmissive mirror 68. The additional illumination window 72 through which the first light source 74 illuminates the sample 98 is therefore advantageous. For a transmission sensor, the first light source 74 for illuminating the material to be measured (sample 98) is typically arranged opposite the window 66 and irradiates the sample 98. Such a measurement geometry restricts the usage flexibility of the measuring head 62, because a corresponding geometry must be established in every installation location. A measurement by reflection offers a higher flexibility, because the measuring head 62 can be arranged on one side with the spectrometer 70 and the first light source 74. A geometry in which the illumination window 72 and the window 66 enclose an angle, e.g. 45°, is also possible for operating the measuring head 62, however (cf. FIG. 2). Thereby a combined reflection and transmission measurement is carried out. The window 66 and the illumination window 72 can also enclose a smaller angle than that shown in FIG. 2 or run parallel to one another, which would mean a pure reflection measurement of the sample 98.

If the spectral range of a single spectrometer 70 is not sufficient, then the measuring head 62 can also be equipped with an additional spectrometer 70', an additional, second light source 76' and an additional standard 78', all of which can be mounted offset about the central axis of the window 66 in relation to the first spectrometer 70, the first light source 76 and the standard 78, as shown in FIG. 3. The spectral ranges covered by the two spectrometers 70, 70' can (but need not) partially overlap, which enables the use of overlapping spectral ranges in one possible embodiment to provide a reference for the measurement values of one of the spectrometers 70, 70' in relation to the measurement values of the other spectrometer 70, 70'. Two spectrometers 70, 70' with identical spectral ranges can also be used, each being used only for simultaneous measurement of different parts of the spectral ranges, to accelerate the measurement.

FIG. 4 shows a second embodiment of a measuring head 62, which is likewise depicted along the line 2-2 of FIG. 1, although the measuring head 62 could be rotated by any desired angle about the vertical axis relative to the sample 98. In the second embodiment, the first light source 74 is accommodated in the housing 64 of the measuring head 62, so that the additional illumination window 72 of FIG. 2 is superfluous. The partially transmissive mirror 68 is arranged outside the light cone of the first light source 74 and the mirror 68 is moved closer to the spectrometer 70. The arrangement of the second light source 76, the standard 78 and the filter 80 is shifted somewhat, but functionally corresponds to that according to FIG. 2.

As explained above, the spectrometer 70 in the illustrated embodiments is designed as a micro-electromechanical system (MEMS). Spectrometers that have been previously used in agricultural technology on the other hand have been equipped with a dispersive grating for decomposing the light reflected from the sample into the spectral components and with a multichannel diode array (Si or InGaAs) for detecting the light. These conventional spectrometers are cost-intensive, because they also include an optical system composed of multiple lenses in addition to the above-mentioned elements of a grating and a detector array. The costs have previously restricted the possibilities for using content substance measurement to high-value agricultural machines (forage harvesters, combine harvesters) or required a flexible system in which one sensor can be mounted on different machines. The systems known as MEMS spectrometers (as described for example in S. Hintschich, MEMS-Based Miniature Near-Infrared Spectrometer for Application in Environmental and Food Monitoring, Proceedings of the 8th International Conference on Sensing Technology, Sep. 2-4, 2014, Liverpool, UK, or T. Pügner et al., Near-Infrared Grating Spectrometer for Mobile Phone Applications, Appl. Spectrosc. 2016, 70(5), 734-745 or DE 10 2007 011 324 A1 or EP 1637850 A1, the disclosures of which documents are hereby incorporated into the present document by reference) are substantially more economical.

A stable and fast measurement (at measuring frequencies on the order of 1 Hz) of inhomogeneous, to some extent granular media such as grain corns or grass or corn choppings in a flow of material requires simultaneous measurement of many particles. This requires that the measurement spot from which the spectrometer 70 registers light and uses it for determining the content substances must be correspondingly large and that it can be illuminated as homogeneously as possible to obtain a representative measurement for the material by a single measurement. If a measurement spot that is too small is used, then the measured spectrum, and thus the measurement result, is changed with every single measurement, because the presentation of the sample in front of the measuring window continuously changes. Then it is necessary to take the average of many single measurements to obtain an average value spectrum representative of the sample. This lowers the measuring frequency. With a sufficiently large measuring spot, the continuous changing of the sample presentation has less of an effect, because an optical averaging takes place. Typical measuring spots for measuring grain in the material flow have a diameter of 3-5 cm for example.

Independently of the design (e.g. as a Fabry Perot or a Michelson interferometer), MEMS spectrometers have low light conductivity values at the input, because they have a small sensitive surface area (a single diode as sensor 102), and offer small numerical apertures at the input, because the internal optical elements demand a strong directional characteristic of the light. Because the material to be examined has a diffusely radiating surface (the light is reflected equally strongly in all directions) and due to the small light conductivity values of the MEMS spectrometer, it is advisable to provide a sufficient distance between the spectrometer 70 and the sample 98. Although it would be possible to reduce this distance by a system of lenses, light is then lost and the sample 98 must be more strongly illuminated. To keep the costs of the measuring head 62 as low as possible, it is also undesirable to add additional lenses to the system. The surface area observed by the spectrometer 70 can be enlarged by having the spectrometer 70 view the measuring spot obliquely (angle α), as shown in FIG. 2.

It should be additionally noted that the standard 78 can also be designed as a non-diffusely reflecting standard. Then the second light source 76 is installed such that light source 76, standard 78, window 66 with mirror 68 and spectrometer 70 each lie in a separate optical path. The second light source 76 can also be directly combined with the standard 78 if the light source 76 radiates through the standard 78, for example. It is also possible to provide a black reference, by designing the measuring channel to be nonreflective in the relevant spectral range such that no external light can enter and a black measurement is performed when no measuring material is present in front of the window 66 and the light sources 74 and 76 are switched off. It is likewise possible to operate the second light source 74 at different intensities to illuminate the standard 78 with different intensities. By recording several spectra at different intensities, the linearity of the spectrometer 70 (i.e. of the sensor 102) can be checked and corrected if necessary.

Alternatively, or additionally, the standard 78 can be designed as a wavelength standard or as a combined white and wavelength standard to additionally enable checking of individual wavelengths. The combined white and wavelength standard consists of a white standard over a certain proportion of its surface and of a wavelength standard over the remaining portion (e.g. semicircles or rectangles side-by-side). One or more filters 80 between the second light source 76 and the standard 78 and/or between the standard 78 and the partially transmissive mirror 68 can be connected in such a manner that light only strikes one of the standards 78 or is passed through the mirror 68 in each case. In that way, separate wavelength and white references can be provided. In measuring operations with the embodiments according to FIGS. 2 and 4, the filter 80 also blocks all light that could strike the standard 78 through the window 66 and be reflected from there back to the spectrometer 70.

The measuring head 62 could additionally have multiple positions for the installation of the spectrometer 70, which are all directed at the same measuring spot. It is therefore possible, depending on the application case or the required measuring accuracy, to equip the sensor with one or more MEMS spectrometers, each of which covers different spectral ranges.

Finally, the measuring head 62 could also comprise an internal acceleration sensor. With such a sensor, it is possible to perform certain operations, e.g. the reference provision, only if the accelerations at the acceleration sensor do not exceed a threshold value.

The invention claimed is:

1. A spectrometric measuring head for forestry, agricultural and food industry applications, comprising:
    a housing having a window and a spectrometer that is arranged inside the housing and comprises a dispersive element and a sensor,
    a first light source for exposing a sample to a first light, which reaches the spectrometer through the window after having been transmitted from the first light source through the window and reflected by the sample, and
    a standard configured to be exposed to a second light to provide a reference for the spectrometer,
    wherein the standard is configured to be exposed to the second light by a second light source arranged in the housing, and the first light source and the second light source are connected to a controller which is operable in normal measuring operation to switch on the first light source and switch off the second light source such that the spectrometer receives the first light, and is operable to switch off the first light source and switch on the second light source in order to provide the second light that is reflected to the spectrometer.

2. The spectrometric measuring head according to claim 1, wherein the first light source is arranged inside or outside the housing.

3. The spectrometric measuring head according to claim 2, wherein a partially transmissive mirror is arranged on the window or between the window and the spectrometer and is configured to reflect the second light reflected from the standard into the spectrometer.

4. The spectrometric measuring head according to claim 2, wherein a filter having an electrically controllable transmissivity is arranged between the second light source and the spectrometer and between a mirror and the standard.

5. The spectrometric measuring head according to claim 2, wherein the spectrometer is designed as a micro-electro-mechanical system.

6. The spectrometric measuring head according to claim 2, wherein an optical axis of the spectrometer encloses an angle different from zero with respect to surface normal lines of the window.

7. The spectrometric measuring head according to claim 2, having at least one additional spectrometer arranged in a housing and offset relative to the spectrometer.

8. The spectrometric measuring head according to claim 1, wherein a partially transmissive mirror is arranged on the window or between the window and the spectrometer and is configured to provide an optical transmission for the first light reflected by the sample toward the spectrometer and is configured to reflect the second light reflected from the standard into the spectrometer.

9. The spectrometric measuring head according to claim 3, wherein a filter having an electrically controllable transmissivity is arranged between the second light source and the spectrometer and between a mirror and the standard.

10. The spectrometric measuring head according to claim 3, wherein the spectrometer is designed as a micro-electro-mechanical system.

11. The spectrometric measuring head according to claim 3, wherein an optical axis of the spectrometer encloses an angle different from zero with respect to surface normal lines of the window.

12. The spectrometric measuring head according to claim 1, wherein a filter having an electrically controllable transmissivity is arranged between the second light source and the spectrometer and between a mirror and the standard.

13. The spectrometric measuring head according to claim 12, wherein the spectrometer is designed as a micro-electromechanical system.

14. The spectrometric measuring head according to claim 12, wherein an optical axis of the spectrometer encloses an angle different from zero with respect to surface normal lines of the window.

15. The spectrometric measuring head according to claim 1, wherein the spectrometer is designed as a micro-electromechanical system (MEMS).

16. The spectrometric measuring head according to claim 1, wherein an optical axis of the spectrometer encloses an angle different from zero with respect to surface normal lines of the window.

17. The spectrometric measuring head according to claim 1, having at least one additional spectrometer arranged in a housing and offset relative to the spectrometer.

18. The spectrometric measuring head according to claim 17, wherein the spectrometer and the at least one additional spectrometer have identical, partially overlapping or different spectral measuring ranges.

19. An agricultural machine having a spectrometric measuring head according to claim 1.

20. A spectrometric measuring head for forestry, agricultural and food industry applications, comprising:
a housing having a window and a spectrometer that is arranged inside the housing and comprises a dispersive element and a sensor,
a first light source for exposing a sample to a first light, which reaches the spectrometer through the window after having been transmitted from the first light source through the window and reflected by the sample, and
a standard configured to be exposed to a second light to provide a reference for the spectrometer,
wherein the standard is configured to be exposed to the second light by a second light source arranged in the housing, and the first light source, the second light source, and a filter are connected to a controller which is operable in normal measuring operation to switch on the first light source and switch the filter to be non-transmissive such that the spectrometer receives the first light and the second light is blocked by the filter, and is operable to switch on the second light source and switch the filter to be transmissive in order to provide the second light that is reflected to the spectrometer.

* * * * *